United States Patent
Schoenberg et al.

(10) Patent No.: US 6,377,835 B1
(45) Date of Patent: Apr. 23, 2002

(54) METHOD FOR SEPARATING ARTERIES AND VEINS IN 3D MR ANGIOGRAPHIC IMAGES USING CORRELATION ANALYSIS

(75) Inventors: Stefan O. Schoenberg, Kandel; Michael Bock, Heidelberg; Michael V. Knopp, Sandhausen; Gerhard Laub, Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/651,748

(22) Filed: Aug. 30, 2000

(51) Int. Cl.⁷ ................................................ A61B 5/05
(52) U.S. Cl. .................... 600/419; 600/420; 324/306; 324/309
(58) Field of Search .................... 600/419, 420, 600/410; 324/306, 307, 309

(56) References Cited

U.S. PATENT DOCUMENTS

| | | | | |
|---|---|---|---|---|
| 5,115,812 A | * | 5/1992 | Sano et al. | 324/306 |
| 5,417,213 A | * | 5/1995 | Prince | 600/419 |
| 5,830,143 A | * | 11/1998 | Mistretta et al. | 600/420 |

OTHER PUBLICATIONS

"Processing Strategies for Time–Course Data Sets in Functional MRI of the Human Brain," Bandettini et al., Magnetic Resonance in Medicine, vol. 30 (1993), pp. 161–173.
"Functional MRA Combining 2D MR DSA and Correlation Analysis," Strecker et al., Proceedings ISMRM, Seventh Annual Meeting, Philadelphia, 1999, p. 484.
Volume Rendering and Connectivity Algorithms for MR Angiography, Cline et al. Magnetic Resonance in Medicine, vol. 18, (1991), pp. 384–394.
"Generalized Matched Filtering for Time–Resolved MR Angiography fp Pulsatile Flow," Wang et al., Magnetic Resonance in Medicine, vol. 30, No. 5 (1993), pp. 600–608.
"Vessel Segmentation in 3D MR Angiography Using Time Resolved Acquisition Curves," Mazaheri et al., Proceedings ISMRM, Seventh Annual Meeting, Philadelphia, 1999, p. 2181.

* cited by examiner

*Primary Examiner*—Ruth S. Smith
(74) *Attorney, Agent, or Firm*—Schiff Hardin & Waite

(57) ABSTRACT

In a 3D magnetic resonance angiography (MRA) method, a region of interest, containing a major pulmonary vessel, is defined in an examination subject, and the subject is injected with a contrast agent bolus and a number of 3D magnetic resonance angiography data sets are obtained from the examination subject before, during and after arrival of the bolus in the region of interest. A slice from each of the data sets is selected which contains the region of interest, and an average region of interest signal as a function of time is determined and stored as a reference time curve. In the respective selected slices, a signal-time curve is identified and each signal-time curve is cross-correlated with the reference time curve. The cross-correlation results are used to form a new three-dimensional data set containing arterial and venous correlation maps. Maximum intensity projections are computed from the arterial and venous correlation maps for producing a visualized image of the pulmonary vasculature in the region of interest, the arteries and veins in the respective maximum intensity projections being clearly distinguishable.

6 Claims, 4 Drawing Sheets

METHOD FOR SEPARATING ARTERIES AND VEINS IN 3D MR ANGIOGRAPHIC IMAGES USING CORRELATION ANALYSIS

BACKGROUND OF THE INVENTION

1. Field of the Invention

The present invention is directed to a method for contrast enhanced MR angiography, and in particular to a method for producing images wherein arteries and veins are clearly visually separated.

2. Description of the Prior Art

Contrast enhanced MR angiography (MRA) is a valuable clinical tool for the evaluation of various types of vascular diseases Prince et al. "3D Contrast MR Angiography," Berlin: Springer, 1997. With the high speed gradient systems available today, image acquisition time of a 3D MRA data set can be reduced to a fraction of a breath hold period. Thus, the arrival, passage and wash-out of a contrast agent bolus can be visualized in a series of MRA data sets, that are acquired in a single breath hold.

Since there is a sequential enhancement of arteries and veins, arterial angiograms with virtually no venous overlay can be acquired if the transit time from the arteries to the neighboring veins is longer than the acquisition time of an MRA data set. Venograms are created from later scans, wherein the signal intensity in the veins is at maximum, but with substantial remaining enhancement of the superimposed arteries. To improve the vessel delineation especially in venograms, a subtraction of arterial from venous data sets can be performed, however, a subtraction increases the noise level in the resultant images. In addition, image subtraction crucially depends on the acquisition of a pure arterial phase, since any venous contamination causes artificial elimination of veins in the subtracted venogram.

In MRI, correlation analysis is typically used with functional imaging of the brain (fMRI), where the signal-time-course at a specific location in the brain is correlated with an external reference function, as described in Bandettini et al., "Processing Strategies for Time-course Data Sets in Functional MRI in the Human Brain, " Magn. Reson. Med. 1993; 30:161–173. Correlation coefficient maps are computed, which are used as an indicator for the strength and the statistical significance of cortical activation. In correlation MRA, the signal-time-course in a selected vessel of interest serves as a reference function. Correlation maps calculated from this reference function highlight structures in the MRA data sets, that show a similar temporal signal behavior as the selected vessel.

Moreover, correlation MRA is a known technique that heretofore has been applied only to two-dimensional projection MRA, where images are sampled at sub-second frame rates as described in Strecker et al., "Functional MRA Combining 2d MR DSA and Correlation Analysis, " Proceedings ISMRM, Seventh Annual Meeting, Philadelphia, 1999, p 484.

Separate arteriograms and venograms can be computed from a single 3D CE-MRA data set by making use of the spatial connectivity of arteries and veins. Good results have been achieved with volume rendering in combination with connectivity algorithms as described in Cline et al., "Volume Rendering and Connectivity Algorithms for MR Angiography," Magn. Reson. Med. 1991; 18: 384–394. Semi-automatic volume rendering, however, can become very time consuming in anatomical regions, where arteries and veins are in close proximity. It also often fails in smaller vessels, where signal levels are comparable with those of the surrounding tissue.

A different approach using matched filtering has been proposed for the separation of arteries from veins in time-resolved ECG-triggered time-of-flight MRA in Wang et al., "Generalized Matched Filtering for Time-Resolved MR-Angiography of Pulsatile Flow, " Magn. Reson. Med. 1993; 30(5):600–608. With matched filtering a set of global or local weighting factors is determined. The resultant arterial or venous image is then formed from the weighted sum of the time-domain data. Mathematically, correlation and matched filtering are very similar, because they can both be described as the product of two vectors. In matched filtering, however, the vectors are formed directly from the data, but correlation first subtracts the temporal average from the data, which intrinsically provides a mechanism for the suppression of static signal.

A separation technique has been described in Mazaheri et al., "Vessel Segmentation in 3D MR Angiography Using Time Resolved Acquisition Curves," Proceedings ISMRM, Seventh Annual Meeting, Philadelphia, 1999, p 2181, that determines the squared Euclidian distance of the local signal-time vector from two given arterial and venous reference vectors (sum of squared differences). To be independent of the signal intensities, the signal-time vector is scaled by a factor that minimizes the squared distance. In a two-dimensional scatter plot of the arterial-venous distance space, arteries and veins form loosely connected islands. Vessel classification is then performed based on a proximity measure in the distance space. This technique is complicated and requires a classification criterion in the two-dimensional feature space and so far it has only been used in MRA studies of the carotid arteries and veins. It has to be evaluated, whether it can be applied to pulmonary MRA.

SUMMARY OF THE INVENTION

It is an object of the present invention to provide a method for conducting MR angiography (MRA) wherein images are produced containing clearly visually separated veins and arteries.

This object is achieved in accordance with the invention in a method wherein the technique of correlation MRA is used to separate lung arteries from lung veins in contrast-enhanced multi-phase 3D MRA data sets, that are acquired at a temporal resolution of several seconds. In the pulmonary vasculature three-dimensional techniques are required, because the arterial and venous vascular trees are arranged in a complex anatomic orientations in space, where projection methods would inevitably suffer from signal superpositions. Using reference signal-time-courses from manually selected regions of interest (ROI) in the main lung arteries and veins, arterial and venous correlation angiograms are computed. For image display, maximum intensity projections are calculated from the correlation data sets and compared to conventional 3D MRA subtraction angiograms.

Initially, region of interest (ROI) is defined in a slice of an examination subject containing either a major pulmonary artery or vein. The average ROI signal as a function of time is then stored as a reference time curve for the subsequent cross-correlation analysis. For each spatial position in the 3D data set, the unnormalized cross-correlation between the reference time curve and the signal-time curve is calculated, negative values are set to zero and the result is stored in a new 3D data set. Subsequently, maximum intensity projections (MIPs) are computed from the arterial and venous correlation maps, to allow visualization of the pulmonary vasculature.

The key issue for time-resolved multi-phase pulmonary angiography is the trade-off in spatial resolution and anatomic coverage for shortening of the acquisition time of each phase. Analysis of pulmonary enhancement kinetics shows that in healthy individuals there is only a short time window of approximately 3s during which only the pulmonary arteries are enhanced (FIG. 1). With increasing acquisition time per phase pulmonary arteries and veins enhance within the same image and it becomes impossible to separate them on the basis of their enhancement kinetics using conventional techniques.

The initially described inventive method using cross-correlation analysis results in even further improved artery and vein separation when multiple boli are administered to the patient in the procedure for obtaining the 3D MRA data set. In particular, a dual bolus procedure has proven effective.

DESCRIPTION OF THE PREFERRED EMBODIMENTS

Figure 1:
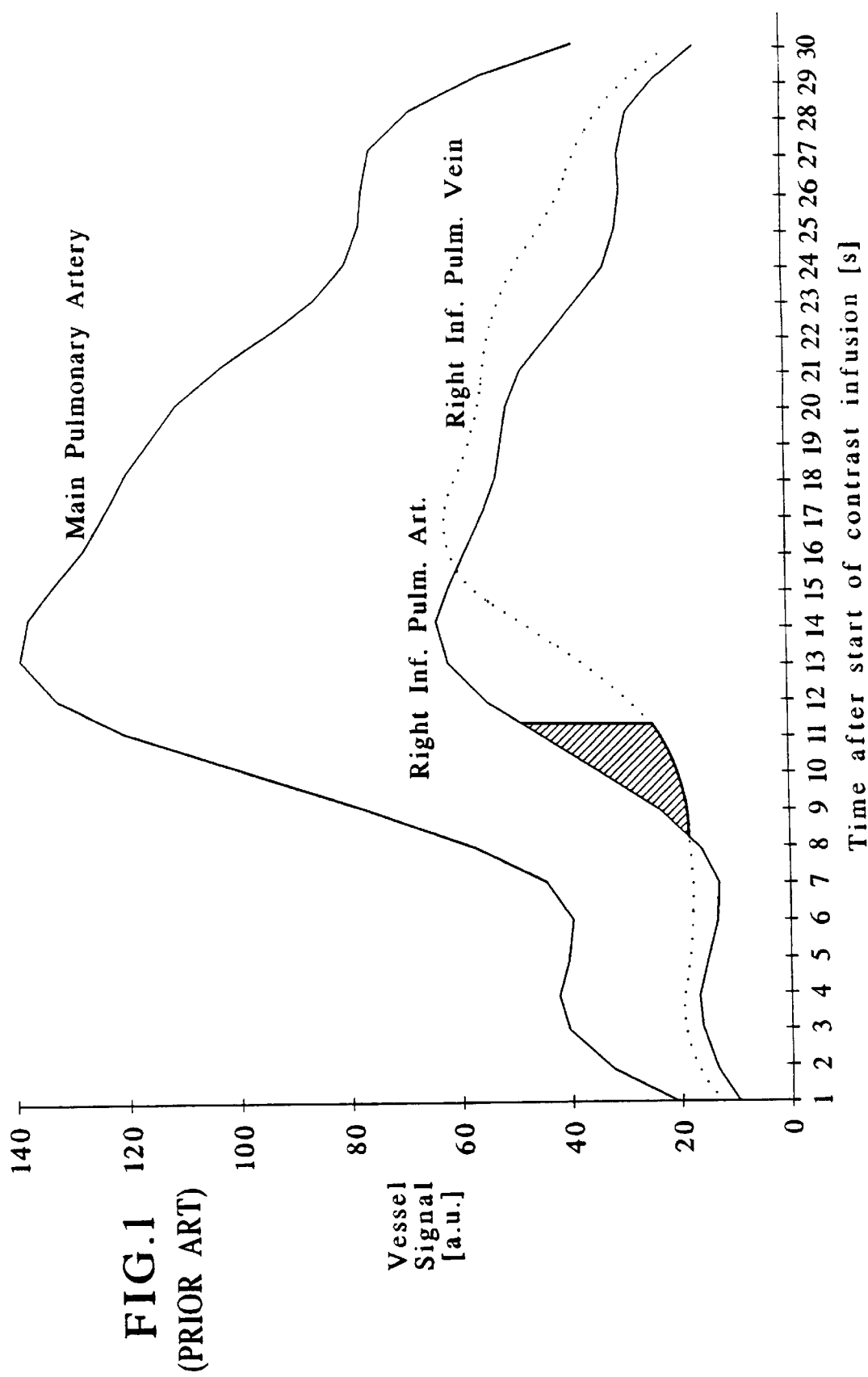
FIG. 1 shows the signal-time curve in the pulmonary vascular system after the infusion of a test bolus of 1 ml gadopentetate at a rate of 3 ml/s.

FIG. 1 shows the signal-time curve in the pulmonary vascular system after the infusion of a test bolus of one ml gadopentetate at a rate of 3 ml/s. As can be seen in FIG. 1, there is only a small time window of about 3 seconds (hatched area) between substantial enhancement of the right inferior pulmonary artery and the corresponding vein. With increasing acquisition time per phase, the pulmonary arteries and veins become enhanced within the same image, and it becomes impossible to separate them on the basis of their enhancement kinetics using conventional techniques. The inventive method employs cross-correlation analysis to address this problem, as well as the other problems noted above associated with MRA.

Correlation analysis allows comparison of a reference function, e.g. a signal-time-course $S_{ref}(t)$, with a target function $S(t)$. The cross correlation coefficient c between these functions is defined as $$c(S_{ref}, S) = \frac{\sum_i (S_{ref}(t_i) - \overline{S_{ref}}) \cdot (S(t_i) - \overline{S})}{r(S_{ref}) \cdot r(S)} \quad (1)$$

with $$r(S_{ref}) = \sqrt{\sum_i (S_{ref}(t_i) - \overline{S_{ref}})^2} \text{ and } r(S) = \sqrt{\sum_i (S(t_i) - \overline{S})^2},$$

if the functions are only known at n discrete time points $t_i (i=1 \ldots n)$. $\overline{S_{ref}}$ and $\overline{S}$ denote the temporal averages of $S_{ref}(t)$ and $S(t)$ taken over all time points. Equation 1 can be interpreted as the scalar product of two n-dimensional vectors $S_{ref}(t_i) - \overline{S_{ref}}$ and $S(t_i) - \overline{S}$ divided by their lengths $r(S_{ref})$ and $r(S)$ (2). Since c is always in the range between −1 and 1, it can be expressed as the cosine of the angle between the vectors. If $S_{ref}(t)$ and $S(t)$ are identical, the angle vanishes and the correlation coefficient is 1, whereas $S_{ref}(t) = -S(t)$ is equivalent to two antiparallel vectors and c=−1. In general, the correlation coefficient will be somewhere between these two extreme cases of perfect positive and negative correlation.

If the term r(S) in the denominator of Eq. 1 is omitted, c'=c·r(S) can be interpreted as the length of the projection of the signal-time vector on the axis of the reference vector. With this modified definition, the cross correlation c' is no longer in the range of −1 to 1. Negative values of c' still indicate, however, that the reference function and the signal-time curve are anti-correlated. If the signal S is constant, c' vanishes, which provides an effective mechanism to suppress static background signal. In the extreme limit of only n=2 data sets, c' is simply proportional to the signal difference $S(t_1) - S(t_2)$.

Contrast-enhanced 3D MRA data sets were acquired from several patients at a 1.5 T whole body scanner (SIEMENS Magnetom VISION, Erlangen, Germany) using the integrated body coil for rf-excitation and a 4-element phased array coil for signal reception. The scanner was equipped with a resonant gradient system providing a maximum gradient strength of 25 mT/m at a rise time of 300 μs.

Gd-DTPA contrast agent (Magnevist®, Schering, Berlin) was injected intravenously with a programmable infusion pump (CAI 626, Doltron, Uster, Switzerland) at a dose of 0.1 ml/kg body weight and an infusion rate of 5 ml/s followed by a flush of 30 ml of saline.

Within a single breath hold between 7 and 8 MRA data sets were acquired with a 3D FLASH pulse sequence (TR/TE/α=3.2 ms/1.1 ms/40°) before, during and after bolus arrival in the lung. Asymmetric k-space sampling was employed in all spatial directions to minimize the acquisition time while maintaining a sufficient spatial resolution. In the readout direction, 160 of 256 raw-data points were acquired starting 32 points before k-space center, while in the phase-encoding, direction 70 of 105 lines were measured, and in the partition encoding direction 12 of 24 k-space lines were sampled. Using a rectangular field of view of 263×350 mm² and a slab thickness of 78 mm a nominal spatial resolution of 2.5×1.4×3.3 mm³ was achieved after zero-filling of the missing k-space information. With these sequence parameters the total acquisition time per 3D data set amounted to 2.9s.

The coronal 3D MRA slab was positioned on sagittal T1-weighted gradient echo localizers. In the anterior to posterior direction, the slab was centered at the main pulmonary veins to encompass as much as possible of the pulmonary vascular tree. To minimize aliasing artifacts in the left to right direction arising from brachial and axillar vessels outside the field of view, radio-frequency absorbing blankets were wrapped around the patients arms. Data acquisition was started with the injection of the contrast agent.

Figure 2:
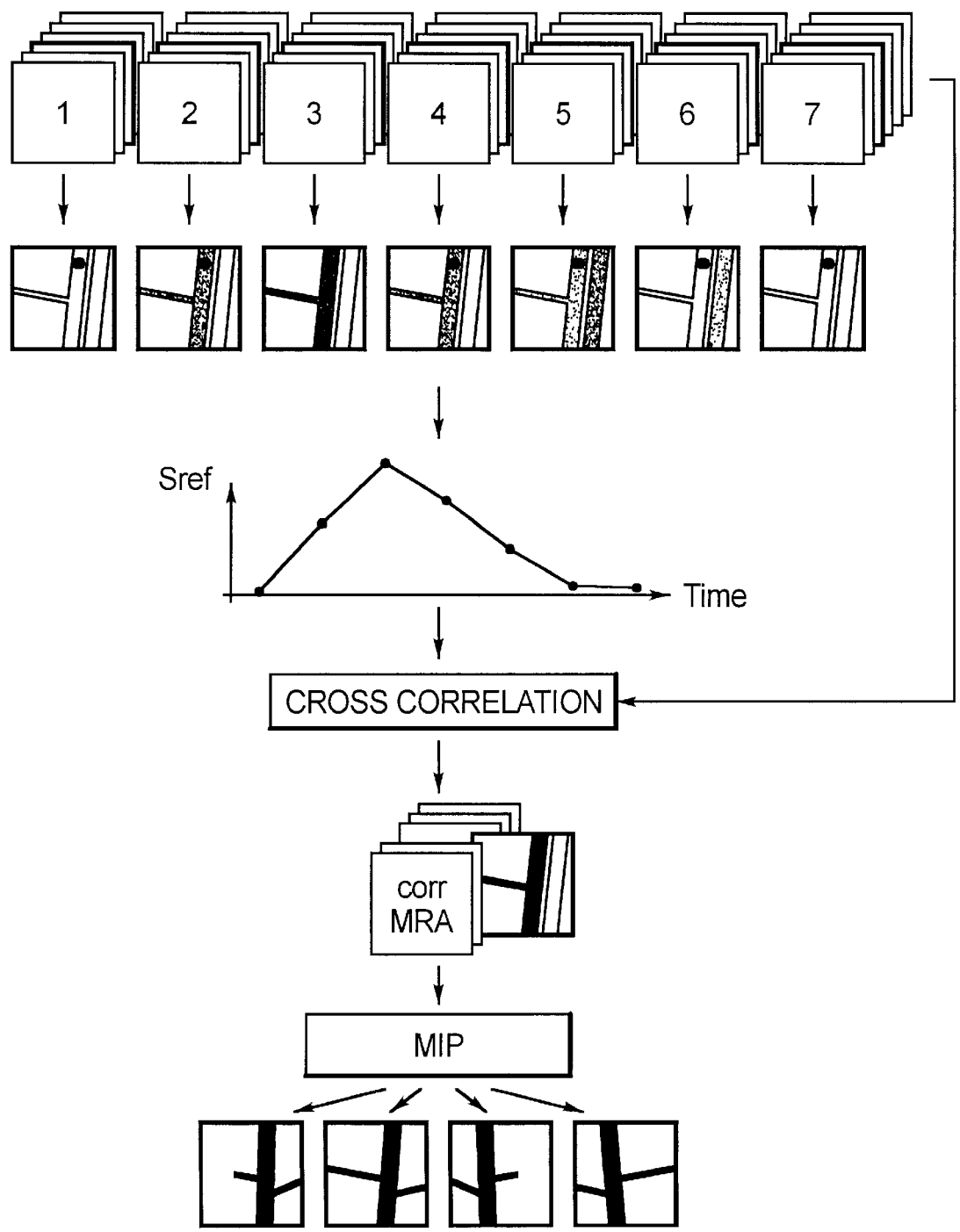
FIG. 2 is a schematic flow chart of the inventive angiography method employing cross-correlation analysis of a series of 3D MRA data sets.

After image acquisition, the 7 to 8 3D MRA data sets were transferred to a separate workstation for calculation of arterial and venous correlation maps. A schematic of the correlation angiography algorithm is shown in FIG. 2. Initially, a region of interest (ROI) is defined in a slice showing either a major pulmonary artery or vein. The average ROI signal as a function of time is then stored as a reference time-curve $S_{ref}(t)$ for the following cross correlation analysis. For each spatial position in the 3D MRA data set, the cross correlation between $S_{ref}(t)$ and the signal-time curve is calculated and the results are stored in a new 3D data set. Finally, maximum intensity projections (MIPs) (four, in this exemplary embodiment) are computed from the arterial and venous correlation maps to visualize the pulmonary vasculature.

The inventive method is based on the expectation from Eq. [1] that in correlation angiograms the static background signal will be suppressed to a high degree (background signal in 3D MRA typically originates from tissues with short $T_1$ relaxation times or from the margins of the 3D slab, where smaller flip-angles are applied than in the center of the slab). Moreover, the subtraction of a pre-contrast image also offers a very simple technique for the suppression of the constant background signal in multi-phase MRA. To compare the conventional difference technique with the inventive correlation analysis technique, difference images between pre-contrast and both peak arterial and peak venous enhancement were computed. From these difference data sets, MIP images were calculated under different projection angles and signal-to-noise ratios (SNR) were determined. Therefore, ROIs were placed in major pulmonary vessels as well as areas that contained only background signal.

The corresponding arterial and venous MIP images of the same subject were compared with the results of an image subtraction. In this case, a very good separation of arteries from veins is achieved with both techniques, because both a peak arterial and a peak venous phase data set were present in the time series. An increased SNR, however, was observed in the correlation images, which enhances the visibility of the more distal pulmonary vessels.

Figure 3:
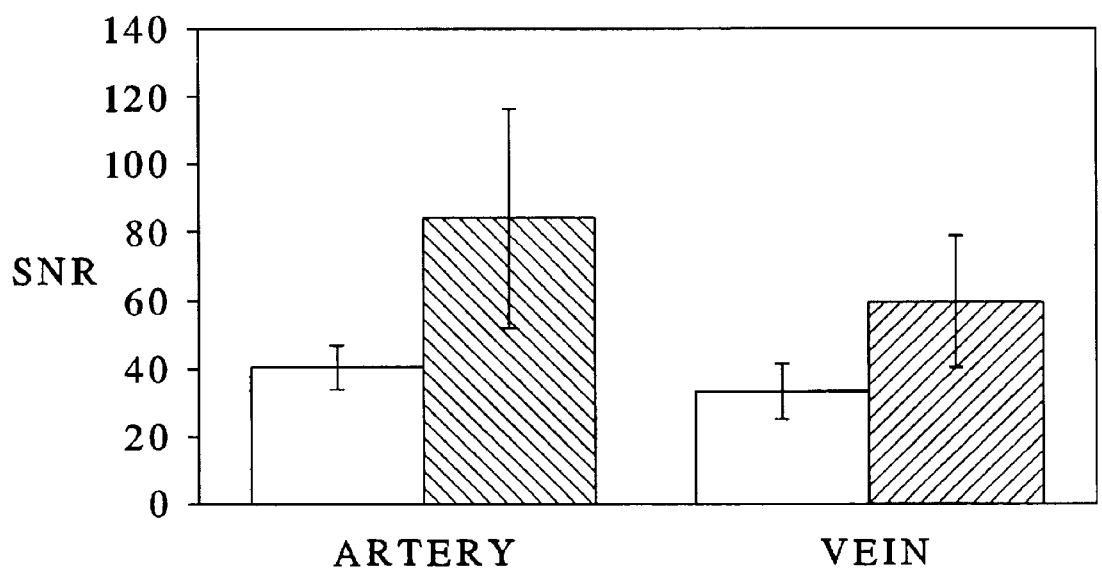
FIG. 3 is a comparison of the signal-to-noise ratios in respective maximum intensity projections (MIPs) calculated using a conventional difference technique ("empty" bar) and using the inventive cross-correlation technique (hatched bar).

FIG. 3 compares the average SNR in the MIP images created with the difference and the correlation technique. The correlation technique has an SNR that is approximately twice as high as the SNR for the difference method in both arterial and venous angiograms. In both techniques a higher SNR was seen in the arterial phase than in the venous phase.

In all acquired data sets a separation of arterial and venous vasculature is possible. The quality of the separation results is found to be dependent on the position of the ROI for the reference signal. Initially, several attempts were needed to find a ROI position yielding a satisfactory arterial or venous angiogram. Later on, ROIs were preferentially placed in the main pulmonary artery for arteriograms or the left or right superior pulmonary vein for venograms.

The inventive method thus provides correlation technique for the generation of pulmonary arteriograms and venograms from multi-phase 3D CE-MRA is presented. In fMRI, cross-correlation was first successfully applied to highlight areas of cortical activation by correlating the stimulus pattern with the signal-time curve of the MR images. In the inventive method, a measured signal-time curve in an arterial/venous vessel is used for reference to selectively suppress both venous/arterial signal as well as unwanted constant background signal.

With the inventive correlation technique, in both arterial and venous projection angiographies the SNR is higher than in the difference angiographies. In general, one must be especially careful when comparing SNRs measured in MIP images, because the maximum intensity projection is a highly non-linear operation. Nonetheless, the result shows that an improved background suppression can be achieved with the inventive correlation technique, because it takes into account all the available 3D data sets, whereas only two data sets are used to generate the difference angiograms. If only two data sets are available, the difference and correlation algorithm would yield identical results (except for an arbitrary scaling factor).

The ability of the correlation algorithm to include all acquired data, however, is not always favorable, because it makes the results prone to artifacts from patient motion. In the study described above, CE-MRA data were sampled over a time span of $(7-8) \times 2.9s = 21-24s$, which is a short enough breath hold period even for patients with lung disease. With longer scan times, motion correction algorithms for image registration might have to be applied to the individual 3D data sets before the correlation coefficients can be calculated.

The inventive correlation algorithm compares the shape of the arterial or venous signal-time curve with the local signal curves. If, e.g., the arrival of the contrast agent bolus in an arterial vessel segment is delayed by a pathological process, its signal-time curve is shifted in time, which results in a higher correlation coefficient with the venous reference function than with the arterial reference function. This problem, which is common to all algorithms that try to identify vessels by their enhancement kinetics, is nevertheless a strength of the inventive technique, because it can allow to pathologic blood vessels to be separated from healthy vessels (e.g. true and false lumina in aneurisms).

If not only one, but several boli of contrast agent are administered during a scan, the enhancement patterns of arteries and veins can be synchronized with the data acquisition in such a way, that their respective signal-time-courses are negatively correlated. In the above example of a pulmonary exam, the scan time per 3D data set thus could be increased to 5–6s, the number of repetitions reduced to four with contrast agent injections before the first and third scan. With the longer scan time per 3D data set a higher spatial resolution or a better anatomical coverage can be achieved.

All dual bolus measurements were performed on a 1.5-T MR system (Magnetom Vision, Siemens Medical Systems Inc., Iselin, N.J.), equipped with a resonant echo planar imaging (EPI) gradient overdrive (maximum gradient strength: 25 mT/m, shortest rise time to maximum: 300 $\mu$s). All exams used the standard 4-element phased-array body coil, centered on the chest. Aliasing from the patient's arm was suppressed by using copper mesh pillows. The pulmonary arteries were localized with $T_1$ weighted FLASH (fast low angle shot) breath hold sequences in coronal and sagittal orientation. Next, multi-phase 3D-Gd-MRA was carried out. The anterior margin of the 3D scan volume was positioned at the middle of the long heart axis. Posteriorly, as much of the pulmonary vasculature as possible was covered within the defined scan volume.

An ultra fast 3D FLASH sequence with asymmetric k-space sampling in readout, phase-encoding and partition direction and a partially self-refocusing radio-frequency pulse was used (TR=2.3 ms, TE=1.1 ms, bandwidth=950 Hz/pixel). In brief, with this sequence only five-eighths of full k-space is acquired starting about one-eighth before k-space center to preserve some high spatial frequency information. A 26×35 cm field-of-view and a 12 cm 3D slab thickness was chosen to be sufficient for anatomic coverage. Within this volume, 90 phase-encoding and 30 partition encoding steps were performed resulting in a voxel size of 1.9×1.4×4.2mm3 after zero-filling and a scan time of 6.28s. In a single breath hold a total of 4 consecutive acquisitions were performed.

Figure 4:
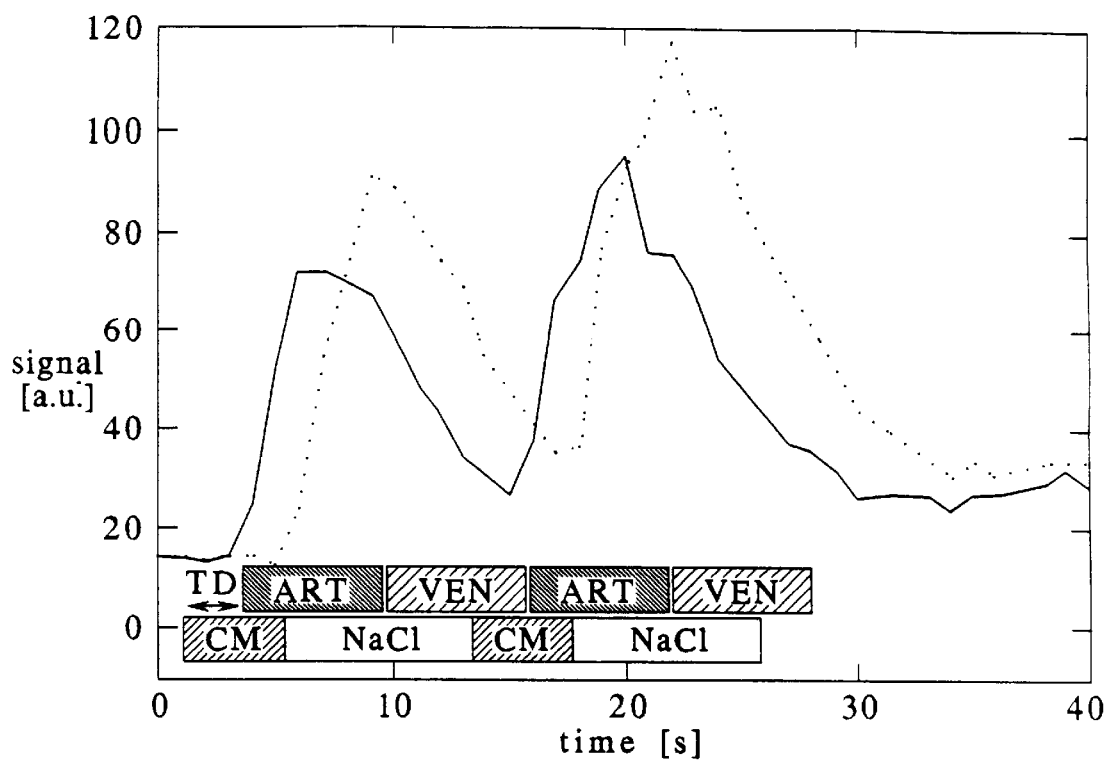
FIG. 4 shows the time sequence of a multiple-bolus multi-phase 3D-Gd-MRA procedure used for obtaining the 3D MRA data set on which cross-correlation is performed in accordance with an embodiment of the inventive method.

The minimum scan time of 6.28s, which still allows adequate anatomic coverage and spatial resolution, is too long to ensure pure arterial phase angiograms without venous overlay. Therefore separation of arteries and veins was further improved by exploiting the intrinsic enhancement kinetics of the pulmonary system. Previous studies have shown that a smaller dose of contrast media administered with higher infusion rates substantially improves the bolus profile with faster onset of peak enhancement and faster complete washout at no cost in maximum signal (see, for example, Schoenberg et al., "Ultrafast MR Venography in the Lungs," Radiologe 1998; 38: 597–605). In a multiphasic acquisition, that is perfectly synchronized with the kinetics of the contrast agent, this can be appreciated as a sequential on-off signal course in the pulmonary arteries and veins. If the fast contrast infusion is repeated several times during the odd number of scan phases, a characteristic signal-time curve for arterial and venous vessel can be obtained. Arterial signal is at maximum directly after contrast media injection, while venous signal is low. In the following image, arterial signal is decreased and veins appear maximally bright. In this study two contrast boli (each 0.1 mmol/kg body weight gadopentetate, Magnevist) were administered by automated infusion (Tomojet CAI, Doltron/Bruker) with an injection rate of 5ml/s, as schematically shown in FIG. 4. To ensure high injection rates and a well-defined bolus profile, at least 16G angiocaths were placed. The repetitive injections were synchronized with the first and third scan phase using programmable delays for the start of the pulse sequence and mechanical infusion. The exact delay time TD between the start of the infusion and the arrival of the contrast bolus in the main pulmonary artery was determined by a test bolus injection of Icc of gadolinium chelate administered during axial single-slice imaging with a TurboFLASH sequence (TR=8.5 ms, TE=4 ms, inversion recovery time=100 ms, 1 image acquired per second). With this design, arterial and venous signal are completely anti-correlated in time, enabling complete separation by means of correlation analysis post-processing, as described above.

The discrimination between vessels with anti-correlating enhancement pattern increases the more time points are available. In fast 2D acquisitions with sub-second acquisition times, hundreds of different time points can be obtained for a particular region of interest. With 3D techniques, only a few time frames are acquired in a breath hold. Nevertheless, the anti-correlating pattern created by the combination of four different times frames and dual-bolus injection proved to be sufficient for arterial and venous correlation maps.

The combined approach of multi-phase angiography, dual-bolus injection and correlation analysis allows the production of pure arteriograms and pure venograms with decent anatomic coverage and a spatial resolution of about 2 mm. In the analysis by a viewer the vessel patency could be evaluated to the level of the segmental vessels. The majority of segmental vessels still revealed the maximum vessel conspicuity score with definitive evaluation of patency. Only the most anterior and posterior vessel segments are not reliably seen. This is related to the limited anatomic coverage of the 3D slab. In addition, cardiac motion substantially affects the assessment of the lingula and left lower lobe vessels. Breathing artifacts were usually considered mild since all patients could hold their breath during the total scan time of 24s. However, this might be biased due to the fact that rather young patients were studied which were not acutely ill. In none of the patients substantial venous overlay occurred in the pulmonary arteriograms.

FIG. 4 shows the timing scheme of the multiple-bolus multi-phase 3D-Gd-MRA concept. The infusion of two contrast agent boli (0.1 mmol/kg body weight at 5 ml/s) is synchronized with the start of the first and third phase (ART) of a multiphasic 3D-Gd-MRA acquisition. A variable time delay (TD) between start of infusion and image acquisition is set to ensure arrival of the contrast media in the pulmonary arteries at the beginning of the first phase and third phase (ART). This time delay is defined by a prior test bolus sequence using 1 ml of contrast (at 5 ml/s). The signal curve for the test bolus in the main pulmonary artery (continues line) as well as the ascending aorta (dashed line) is shown. Each contrast infusion is followed by a continuous flush of normal saline (NaCl). During this time the contrast bolus has been propagated into the pulmonary veins, while the second and fourth phase (VEN) of the multi-phase scan are acquired.

Figure 5:
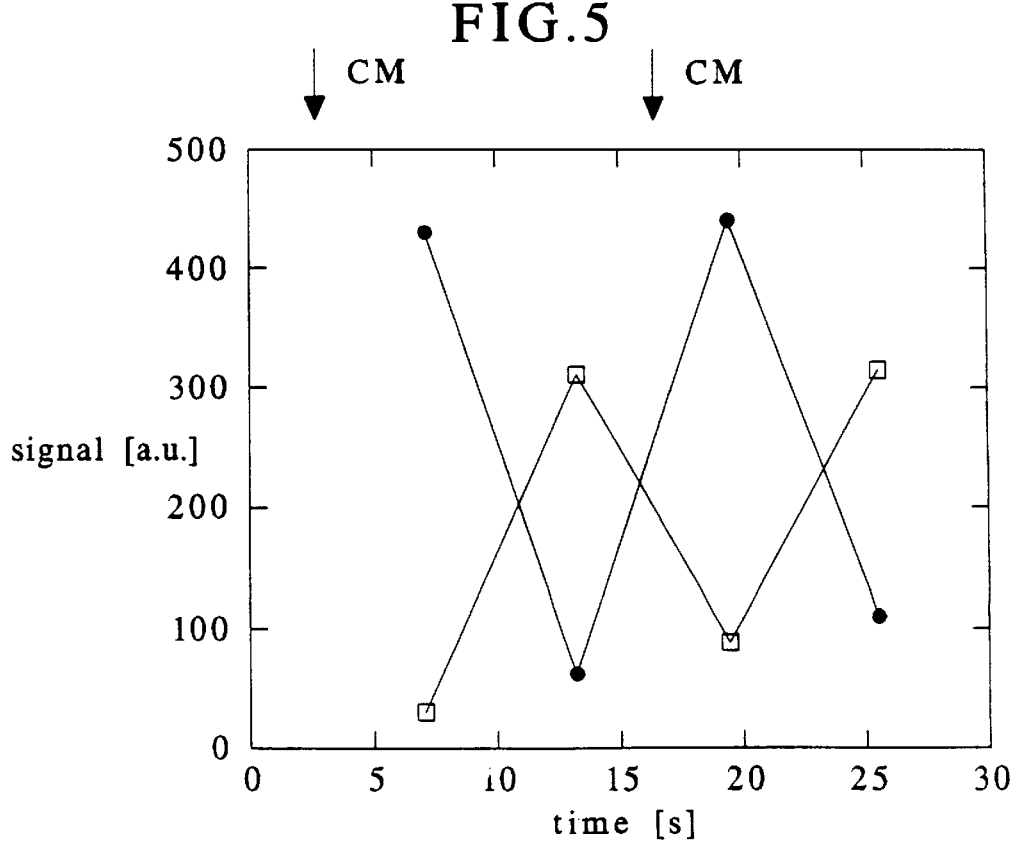
FIG. 5 shows the resulting measured enhancement pattern of pulmonary arteries (•) and veins (□) using the multiple-bolus procedure shown in FIG. 4.

The resulting measured enhancement pattern of pulmonary arteries (•) and veins (□) in a series of four multiphasic images, using the multiple-bolus procedure shown in FIG. 4, is shown in FIG. 5. As can be seen in FIG. 5, in the first and third phase of the multiphasic acquisition (at 6s and 19s after sequence start) the arterial signal is at maximum while the venous signal is low. In the second and fourth phases (at 13s and 25s after sequence start) a reversed pattern is found, and arterial and venous signal-time curves are highly anti-correlated. Overall, a slight increase in baseline signal is noted due to the recirculation of the contrast agent.

Although modifications and changes may be suggested by those skilled in the art, it is the intention of the inventor to embody within the patent warranted hereon all changes and modifications as reasonably and properly come within the scope of his contribution to the art.

We claim as our invention:

1. A 3D magnetic resonance angiography method, comprising the steps of:

defining a region of interest in an examination subject, said region of interest containing a major pulmonary vessel;

injecting a contrast agent bolus into said examination subject and obtaining a plurality of 3D magnetic resonance angiography data sets from said examination subject before, during and after arrival of said bolus in said region of interest;

selecting a slice from each of said data sets containing said region of interest;

determining an average region of interest signal as a function of time and storing said average region of interest signal as a reference time curve;

in the respective selected slices from the plurality of data sets, identifying a signal-time curve for the slice;

for each of the selected slices, cross-correlating the signal-time curve obtained from the slice with said reference time curve, to obtain cross-correlation results;

storing said cross-correlation results as a new 3D data set containing arterial and venous correlation maps; and computing maximum intensity projections from said arterial and venous correlation maps for producing visualized images of arterial and venous vasculature in said region of interest.

2. A method as claimed in claim 1 wherein the step of cross correlating said reference time curve and said signal-time curve comprises obtaining a cross-correlation coefficient $c'(S_{ref}, S)$ according to $$c'(S_{ref}, S) = \frac{\sum_i (S_{ref}(t_i) - \overline{S_{ref}}) \cdot (S(t_i) - \overline{S})}{r(S_{ref})}$$

with $$r(S_{ref}) = \sqrt{\sum_i (S_{ref}(t_i) - \overline{S_{ref}})^2}$$

and replacing all negative values in said $c'(S_{ref}, S)$ with a value of zero, and wherein $S_{ref}$ is said reference time curve and S is said signal-time curve, and wherein $S_{ref}$ and S are known at discrete time points $t_i$ (i=1...n), and wherein $\overline{S_{ref}}$ is a temporal average of $S_{ref}(t_i)$ and wherein $\overline{S}$ is a temporal average of $S(t_i)$.

3. A method as claimed in claim 1 wherein the step of administering a contrast agent bolus comprises administering multiple contrast agent boli to said examination subject.

4. A method as claimed in claim 3 comprising administering two contrast agent boli to said examination subject.

5. A method as claimed in claim 4 comprising acquiring said 3D magnetic resonance angiography data sets in a four phase magnetic resonance angiography imaging sequence.

6. A method as claimed in claim 5 comprising the steps of:
   administering a first contrast agent bolus to said examination subject at a start time, and administering a second contrast agent bolus at a second time following said start time;
   beginning a first phase of said magnetic resonance angiography sequence, for imaging pulmonary arteries, following a predetermined time delay after said start time, and ending said first phase before said second time;
   starting a second phase of said magnetic resonance angiography sequence, for imaging pulmonary veins, after ending said first phase and before said second time;
   beginning a third phase of said magnetic resonance angiography sequence after an end of said second phase, and after said second time; and
   beginning a fourth phase of said magnetic resonance angiography sequence after an end of said third phase, and after said second time.

\* \* \* \* \*